United States Patent [19]
Levine et al.

[11] Patent Number: 6,074,407
[45] Date of Patent: Jun. 13, 2000

[54] DELIVERY CATHETER FOR OCCLUSIVE IMPLANTS

[75] Inventors: Marc-Alan Levine, Belmont; Michael P. Wallace, Pleasanton, both of Calif.

[73] Assignee: Target Therapeutics, Inc., Fremont, Calif.

[21] Appl. No.: 08/950,002

[22] Filed: Oct. 14, 1997

[51] Int. Cl.$^7$ .................................................. A61M 29/00
[52] U.S. Cl. .............................................................. 606/194
[58] Field of Search .................................. 606/194, 195, 606/191, 192, 213

[56] References Cited

U.S. PATENT DOCUMENTS

| | | |
|---|---|---|
| 4,739,768 | 4/1988 | Engelson . |
| 4,813,934 | 3/1989 | Engelson et al. . |
| 4,838,879 | 6/1989 | Tanabe et al. . |
| 4,850,960 | 7/1989 | Grayzel ................................. 606/194 |
| 4,884,579 | 12/1989 | Engelson . |
| 4,994,069 | 2/1991 | Ritchart et al. . |
| 5,033,998 | 7/1991 | Corday et al. . |
| 5,122,136 | 6/1992 | Guglielmi et al. . |
| 5,135,494 | 8/1992 | Engelson et al. . |
| 5,171,221 | 12/1992 | Samson . |
| 5,234,437 | 8/1993 | Sepetka . |
| 5,250,071 | 10/1993 | Palermo . |
| 5,261,916 | 11/1993 | Engelson . |
| 5,304,195 | 4/1994 | Twyford, Jr. et al. . |
| 5,304,198 | 4/1994 | Samson . |
| 5,312,415 | 5/1994 | Palermo . |
| 5,324,259 | 6/1994 | Taylor et al. . |
| 5,334,143 | 8/1994 | Carroll . |
| 5,348,537 | 9/1994 | Wiesner et al. . |
| 5,350,397 | 9/1994 | Palermo et al. . |
| 5,354,295 | 10/1994 | Guglielmi et al. . |
| 5,364,354 | 11/1994 | Walker et al. .......................... 606/194 |
| 5,429,605 | 7/1995 | Bernd et al. . |
| 5,437,632 | 8/1995 | Engelson . |
| 5,454,788 | 10/1995 | Walker et al. . |
| 5,522,836 | 6/1996 | Palermo . |
| 5,573,508 | 11/1996 | Thornton . |
| 5,658,264 | 8/1997 | Samson . |
| 5,669,931 | 9/1997 | Kupiecki et al. . |
| B1 4,739,468 | 11/1994 | Engelson . |
| B2 4,739,768 | 10/1995 | Engelson . |

FOREIGN PATENT DOCUMENTS

| | | |
|---|---|---|
| 0 664 104 A2 | 7/1995 | European Pat. Off. . |
| 0 769 307 A2 | 4/1997 | European Pat. Off. . |
| 2 696 636 | 4/1994 | France . |
| WO 93/16650 | 9/1993 | WIPO . |
| WO 97/21462 | 6/1997 | WIPO . |
| WO 97/27893 | 8/1997 | WIPO . |

*Primary Examiner*—Todd E. Manahan
*Attorney, Agent, or Firm*—Morrison & Foerster, LLP

[57] ABSTRACT

This is a catheter device for delivering vaso-occlusive materials or devices to a desired site with the body. The catheter is a single lumen valved balloon catheter that enhances the accurate placement of the vaso-occlusive material or device. The balloon may be positioned such that it blocks the opening to a vascular malformation such as an aneurysm. In one embodiment, the balloon is automatically inflated as the vaso-occlusive material or device engages a constrictive feature near the distal end as the device is discharged. The catheter device may also have a lengthened distal section that may be placed within the malformation or aneurysm to improving the filling capability of the device. The catheter device may be constructed to have a number of advantageous radioopaque markers to aid in accurately discharging the vaso-occlusive material or device.

21 Claims, 7 Drawing Sheets

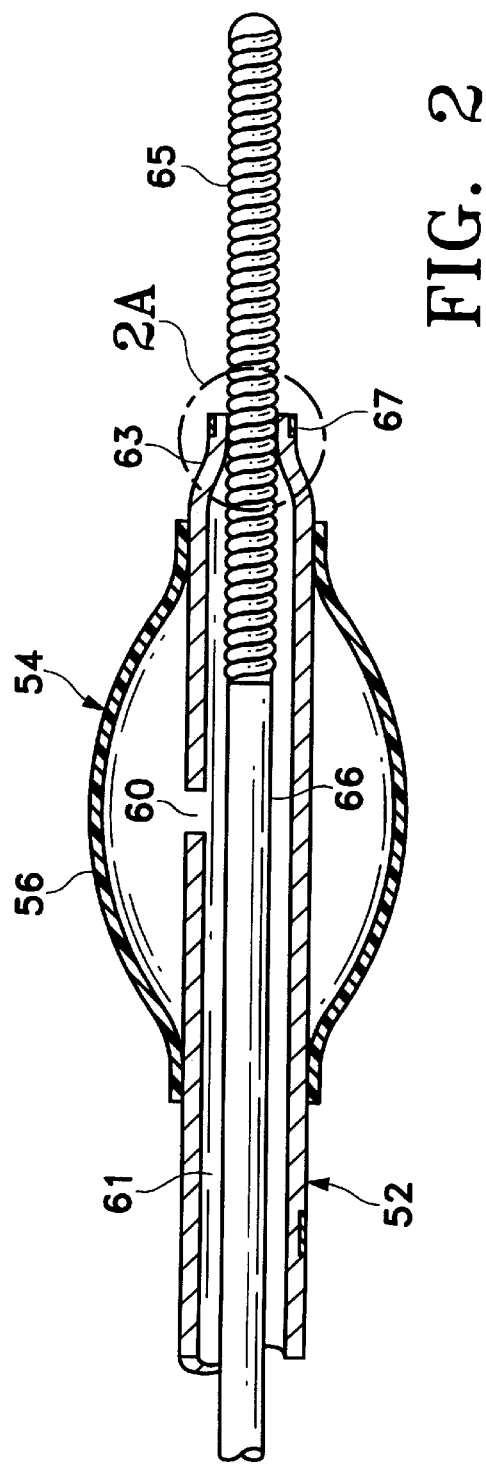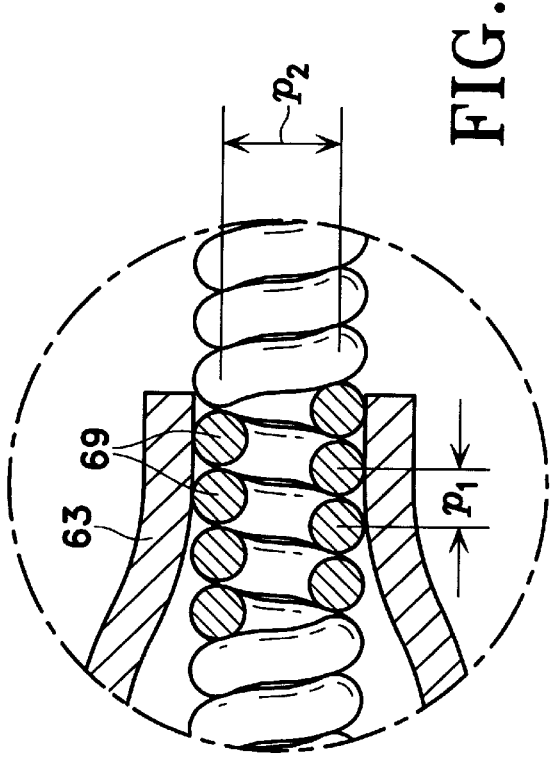

DELIVERY CATHETER FOR OCCLUSIVE IMPLANTS

FIELD OF THE INVENTION

This invention is in the general field of surgical instruments and relates specifically to a single lumen valved balloon catheter for delivering occlusive implants to a desired site in a mammal.

BACKGROUND OF THE INVENTION

Endovascular therapy has been used to treat a variety of different conditions, including control of internal bleeding, occlusion of blood supply to tumors, and relief of vessel wall pressure in the region of an aneurysm. Such therapeutic treatments typically require the use of a catheter to place various treatment materials, devices, and drugs at remote locations within the body. Microcatheters, such as those shown by Engleson, *"Catheter Guidewire"*, U.S. Pat. No. 4,884,579 and as described in Engleson, *"Catheter for Guidewire Tracking"*, U.S. Pat. No. 4,739,768, allow navigation through the body's tortuous vasculature to access such remote sites as the liver or the cerebral arteries of the brain.

For certain maladies, such as vascular malformations and aneurysms, it may be required to create an endovascular occlusion at the defect site. A catheter is typically used to place a vaso-occlusive device or agent within the vasculature of the body to either block the flow of blood through a vessel making up that portion of the vasculature by forming an embolus or by forming such an embolus within an aneurysm stemming from the vessel. In the case of an aneurysm in a parent vessel or artery, for example, the distal end of a delivery catheter is placed within the aneurysm and a suitable vaso-occlusion material or device is delivered through the distal end of the catheter and into the aneurysm, thus forming the desired embolus.

Formation of the embolus may involve the injection of a fluid embolic agent such as microfibrillar collagen, Silastic beads, or polymeric resins such as cyanoacrylate. Ideally, the embolizing agent adapts itself to the irregular shape of the internal walls of the malformation or aneurysm. One risk with this procedure is inadvertent embolism in the parent artery due to the inability to contain the fluid agent within the aneurysm. This is especially true when the opening to the aneurysm is relatively large.

Mechanical vaso-occlusive devices are also well known. One widely used vaso-occlusive device is a wire coil or braid which can be introduced through a delivery catheter in a stretched linear form and which assumes an irregular shape upon discharge of the device from the end of the catheter to engage and fill an opening such as an aneurysm.

For instance, U.S. Pat. No. 4,994,069 to Ritchart et al., shows a flexible, preferably coiled, wire for use in a small vessel vaso-occlusion. Ritchart teaches a coil which is fairly soft that may be delivered to the site using a catheter and pusher. The catheter may be guided to the site through the use of a guidewire (see U.S. Pat. No. 4,884,579) or by flow-directed means such as a balloon placed at the distal end of the catheter. Once the site has been reached, the catheter lumen is cleared by removing the guidewire (if a guidewire has been used), and one or more coils are placed into the proximal open end of the catheter and advanced through the catheter with a pusher. The pusher is typically a wire having a distal end adapted to engage and push the coil through the catheter lumen as the pusher itself is advanced through the catheter. Once the coil reaches the distal end of the catheter, it is discharged from the catheter by the pusher into the vascular site.

The Ritchart et al. coils are typically pushed into the desired vascular site in a linear configuration. Upon discharge from the catheter, the coil may undertake any of a number of random or regular configurations designed to fill the site. The coils are relatively permanent, can be easily imaged radiographically, and may be retrieved.

In addition to using a pusher as described in Ritchart, the vaso-occlusive coils may be discharged from the catheter in a variety of other ways. U.S. Pat. Nos. 5,354,295 and 5,122,136, both to Guglielmi et al., describe an electrolytically detachable embolic device. U.S. Pat. No. 5,234,437, to Sepetka, shows a method of unscrewing a helically wound coil from a pusher having interlocking surfaces. U.S. Pat. No. 5,250,071, to Palermo, shows an embolic coil assembly using interlocking clasps mounted both on the pusher and on the embolic coil. U.S. Pat. No. 5,261,916, to Engelson, shows a detachable pusher-vaso-occlusive coil assembly having an interlocking ball and keyway-type coupling. U.S. Pat. No. 5,304,195, to Twyford et al., shows a pusher-vaso-occlusive coil assembly having an affixed, proximately extending wire carrying a ball on its proximal end and a pusher having a similar end. The two ends are interlocked and disengage when expelled from the distal tip of the catheter. U.S. Pat. No. 5,312,415, to Palermo, also shows a method for discharging numerous coils from a single pusher by use of a guidewire which has a section capable of interconnecting with the interior of the helically wound coil. U.S. Pat. No. 5,350,397, to Palermo et al., shows a pusher having a throat at its distal end and a pusher through its axis. The pusher sheath will hold onto the end of an embolic coil and will then be released upon pushing the axially placed pusher wire against the member found on the proximal end of the vaso-occlusive coil. Finally, U.S. Pat. No. 5,669,931 shows hydraulic discharge of embolic coils. In a preferred embodiment, the coils are provided in an introducer cartridge.

Regardless of the manner of discharge, many embolic coils are subject to the same placement risk as that of fluid embolic agents. That is, as the length of coil is discharged from the distal end of the catheter into an aneurysm, for example, it is difficult to ensure that the coil is contained within the open space of the aneurysm. For example, the distal end or an intermediate section of the discharged coil may be deflected or routed back through the opening to the aneurysm as the coil proceeds to conform to and fill the open space within the aneurysm.

There is a need for a delivery system which overcomes the limitations described above. More specifically, there is a need for a catheter for delivering vaso-occlusive materials or devices which can control the placement of the materials or devices upon discharge from the catheter. The delivery catheter must have a small diameter and have a highly flexible construction which permits movement along a small-diameter, tortuous vessel path.

SUMMARY OF THE INVENTION

This invention is a catheter for delivering vaso-occlusive materials or devices to a desired site within a body. In one aspect of the invention the catheter is a single lumen valved balloon catheter which is inflated as the vaso-occlusive device is discharged from the catheter lumen. In another aspect of the present invention, a catheter is provided with a number of radioopaque markers that allow improved radiographic imaging during use. The invention may also involve a method of treating a vascular malformation using the inventive catheter.

The invention may involve a catheter device for delivering a vaso-occlusive member where the catheter has an inner lumen, an inflatable balloon in fluid communication with said lumen, and a tip section extending from the balloon to the distal end of the catheter. An elongated vaso-occlusive member may be positioned within the lumen and is slidable therein and is deliverable to a site within the body through the distal end of the tip section. The outside diameter of the vaso-occlusive member is sized to engage the inside diameter of the lumen within the tip section to at least partially block the lumen, thus causing fluid supplied through the lumen to be forced into and inflate the balloon.

The inside diameter of the lumen in the area of the tip section is preferably less than the outside diameter of the vaso-occlusive member. In a preferred embodiment, the inner diameter is about 0.001 to 0.003 inches smaller than the outer diameter of the vaso-occlusive member. A decreased diameter in the tip area may be created using a annular band positioned around the exterior of the tip section. When the inside diameter of the tip section is configured to be smaller than the outside diameter of the vaso-occlusive member, it may be preferable to construct the tip to be sufficiently flexible to allow the vaso-occlusive coil to be discharged without requiring excessive axial force.

The tip section may typically have a length greater than 1 cm and but may be cut or trimmed to yield the desired length depending on the preference of the operating surgeon. The tip section may be shapeable, for instance using steam.

According to another aspect of the present invention, a catheter for delivering a vaso-occlusive member may have an inner lumen adapted to slidably receive a vaso-occlusive coil and is constructed with a plurality of marker pairs separated by a fixed distance. According to one embodiment, each marker pair comprises a distal marker and a proximal marker separated by a distance substantially equal to the length of the coil to be inserted. Each marker pair is incrementally spaced from one another starting from the distal end of the catheter. The incremental spacing may be from about 2.0 mm to about 10.0 mm.

The present invention may also involve a method of treating a vascular malformity using a vaso-occlusive member. The method generally comprises the steps of: (a) accessing a malformity within the body using a catheter having an inner lumen, and inflatable balloon in communication with said lumen, and a distal tip section having associated therewith a plurality of markers; (b) positioning the catheter such that at least a portion of the distal tip section is within the malformity and positioning said balloon such that when it is inflated it will substantially occlude the opening to the malformity; (c) introducing a vaso-occlusive member into said lumen; and (d) substantially simultaneously discharging the coil such that the balloon is inflated. The method is particularly useful for treatment of terminal and berry aneurysms. The method may also involve cutting the length of the tip section according to the size of the vasculature to be accessed or the size of the malformity to be treated.

BRIEF DESCRIPTION OF THE DRAWINGS

FIG. 2 shows a partial cross-sectional view of one embodiment of the distal region of the inventive catheter.

FIG. 2A shows a detail view of the constricted region as indicated by view line 2A—2A in FIG. 2.

DESCRIPTION OF THE INVENTION

Figure 1:
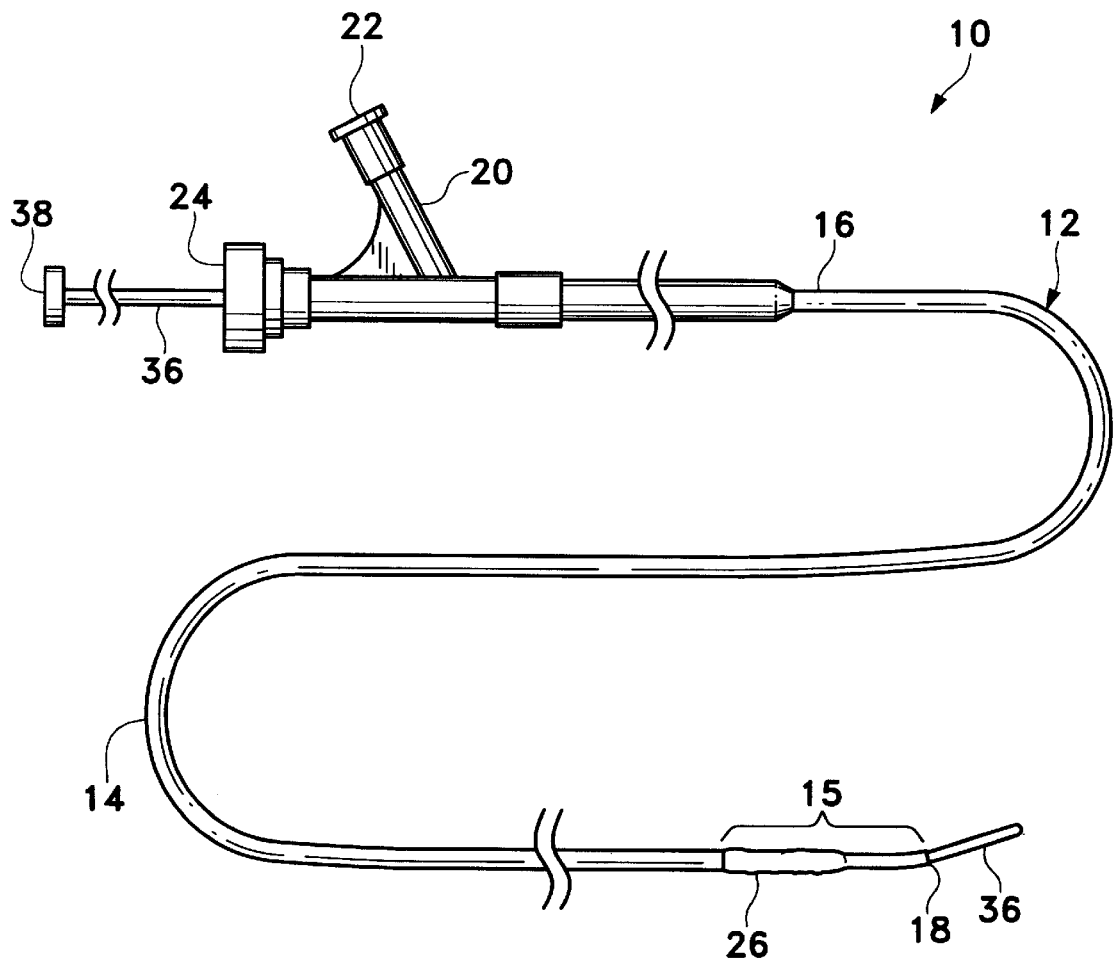
FIG. 1 shows a catheter device constructed according to one embodiment of the present invention.

Referring to the drawings in detail wherein like numerals indicate like elements, the present invention generally involves a catheter for the controlled delivery or discharge of vaso-occlusive materials or implants. The placement of the implant is controlled by way of a single-lumen valved balloon catheter. According to the present invention, the catheter may have a shapeable section distal to the balloon and radioopaque markers positioned to provide improved visualization of the implant during delivery.

FIG. 1 shows a catheter assembly 10 constructed according to one embodiment of the present invention. Catheter assembly 10 includes a catheter 12 composed of a flexible, thin walled body or tube 14 having an inner lumen (not shown) extending between proximal and distal catheter ends 16,18 respectively. Tube 14 may be made from any medically acceptable material, preferably a nondistensible polymer having the appropriate mechanical properties. Preferred materials include polyethylene, polyester, polypropylene, polyimide, polyvinyl chloride, ethylvinyl acetate, polyethylene terephthalate, polyurethane, PEBAX, fluoropolymers, and their mixtures and block or random copolymers. Tube 14 may be a single layer construction or a multiple layer composite construction. Tube 14 may have a spiral wound construction, as shown in U.S. Pat. No. 5,658,264, the entirety of which is herein incorporated by reference or a braided construction, as shown in co-pending U.S. patent application Ser. No. 08/607,847, titled "BRAIDED BODY BALLOON CATHETER", the entirety of which is herein incorporated by reference.

The proximal catheter end 16 is provided with a syringe fitting 20 through which fluid can be supplied to the catheter lumen through a port 22. The fitting includes an axially extending port 24 also communicating with the catheter's inner lumen. Tube 14 preferably has an inner diameter of approximately 0.010–60 mils and walls that are approximately 3–15 mils thick. The total tube length is preferably between about 50–300 cm.

The catheter of FIG. 1 is shown with an optional elongate torqueable guidewire 36 which is constructed to extend through the catheter for axial sliding therein. Optional guidewire 36 may have any suitable construction for guiding the flexible catheter to its intended site within the body. Typically, the length of the guidewire is at least about 10–50 cm longer than the catheter such that the distal end of the guidewire can be extended several centimeters or more beyond the distal end of the catheter, while allowing the proximal end of the wire to be manipulated, such as by torqueing. The proximal end of the guidewire is equipped with a handle 38 for applying torque to the wire during a catheter operation.

The guidewire may have a variable or step diameter along its length, typically including a larger-diameter, stiffer proximal region, and one or more smaller-diameter, more flexible distal end regions, giving the wire good torqueability in its more proximal region, and better flexibility and maneuverability along its more distal region where the wire is advanced along smaller-diameter tortuous pathways. Typical wire dimensions, for a catheter having a lumen diameter of between about 20–50 mils, are a proximal segment extending along all but the last 20–50 cm of wire and having a diameter of between about 18–40 mils, and one or more reduced diameter segments 20–50 cm in length having diameters of between about 8–18 mils. In addition, the distal end portion of the wire may have a substantially constant taper, down to a final wire thickness of about 1–5 mils, for greater distal-end flexibility. This tapered region may be encased in a constant-diameter coil and may terminate in a bent tip to facilitate steering through the vasculature.

The distal end region 15 of catheter 12 is provided with an inflatable balloon 26. According to one aspect of the present invention, balloon 26, when inflated in position, aids in controlling the placement of vaso-occlusive materials or devices by blocking the entrance to the aneurysm. The balloon is preferably about 0.5 to 3 cm in length, and has a wall section which can be inflated by fluid supplied through the catheter lumen when the distal end of the catheter tube is partially blocked in a manner to be described below. The balloon wall section is preferably formed from a thin sleeve of polymeric material and attached at its opposite sleeve ends to relatively more rigid tube sections. Details of the construction of exemplar balloons may be found in co-owned U.S. Pat. Nos. 5,171,221 and 5,135,494 the entirety of each is herein incorporated by reference.

Figure 3:
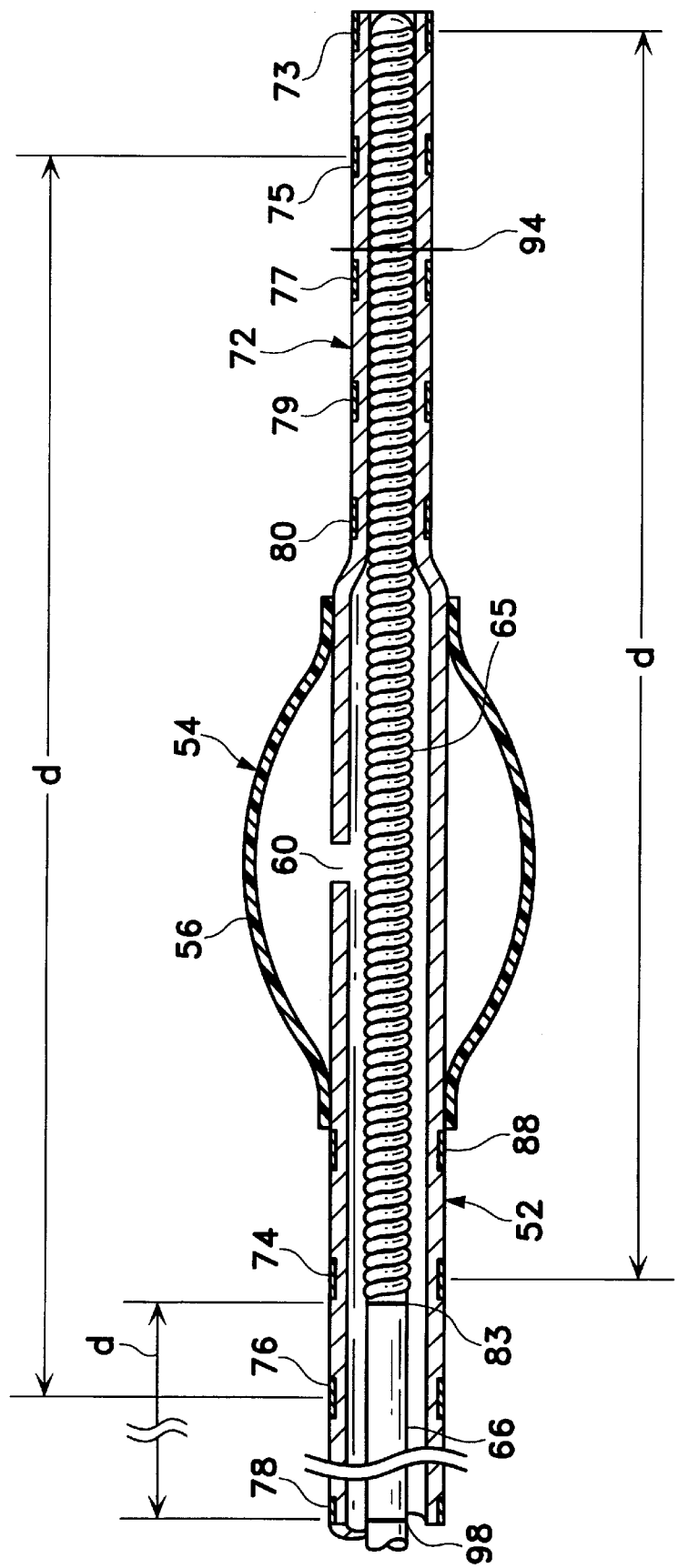
FIG. 3 shows a partial cross-sectional view of an further embodiment of the distal region of the inventive catheter.
Figure 4:
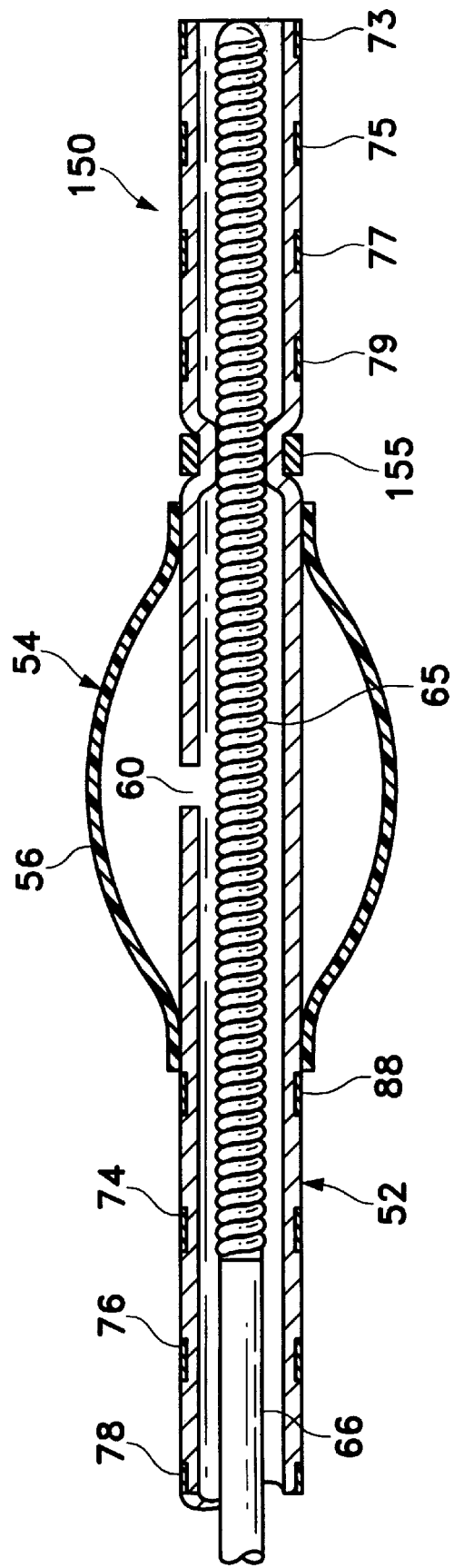
FIG. 4 shows a partial cross-sectional view of an alternate construction of the distal region of the inventive catheter.

FIGS. 2 through 4 illustrate various constructions of the distal end region 15 and balloon 26 of the catheter illustrated in FIG. 1 for the controlled delivery of vaso-occlusive materials or devices. Referring to FIG. 2, catheter tube 52 has an inflatable balloon 54 which is formed by an inflatable sleeve 56 secured at its ends to the catheter wall. The balloon sleeve may be formed of a thin polymer material, and preferably an elastomeric, stretchable material such as silicone rubber, latex rubber, or polyvinyl chloride, or alternatively, a non-stretchable film material such as polyethylene or polypropylene. Attachment of the sleeve ends to the catheter tube is by gluing, heat sealing or the like, or other known methods. One advantage of an elastomeric sleeve is that it tends to remain flush with the tube in an uninflated state, and also tends to deflate itself when the fluid pressure is released. Non-stretchable materials may be preferred in some instances because they require less pressure to inflate.

At least one opening 60 is formed in the catheter tube 52 to provide for fluid communication between the catheter lumen 61 and the balloon 54. Distal to opening 60, is constricted region 63 of catheter tube 52. As pusher 66 discharges vaso-occlusive coil 65 from the catheter lumen 61, coil 65 passes through constricted region 63 to at least partially or completely block catheter lumen 61. When catheter lumen 63 is blocked, any fluid pressure supplied by way of port 22 is communicated to balloon 54 by way of opening 60, thus inflating the balloon. This construction provides for a single lumen catheter having a valve which is inflated simultaneously with delivery of the vaso-occlusive implant to the aneurysm.

The inside surface of catheter tube 52 provides a suitable guide for the delivery of vaso-occlusive implants such as coils using a suitable pusher. The inside diameter of catheter tube 52 in the region before constricted region 63 is generally somewhat larger than that of the expected coil outside diameter. For example the inside diameter in that area may be oversized 0.002 to 0.025 inches or more, preferably about 0.005 to about 0.010 inches.

Constricted region 63 may be constructed to be significantly smaller than the outsided diameter of the vaso-occlusive coil or may be designed to be a close fit. Constricted region 63 typically has a region with an inside diameter which is slightly smaller than the outside diameter of the coil. For example, in a vaso-occlusive coil having an outside diameter of 0.015 inches, the inside diameter of constricted region 63 is between about 0.01 to 0.015 inches, preferably about 0.013 inches. For a vaso-occlusive coil having an outside diameter of 0.010 inches, the inside diameter of the constricted region 63 is sized to be from about 0.007 to 0.010 inches, preferably about 0.009 inches.

Preferably, the wall of the catheter tube in that area is flexible enough to allow the coils to pass through without requiring excessively high axial discharge forces from the pusher, and yet maintain a seal sufficient to facilitate inflation of the balloon. As seen in FIG. 2A, the vaso-occlusive coil may be constructed such that the axial pitch, $p_1$ between successive coils 69 are substantially the same as the wire diameter of the coils 69. Some amount of deviation is acceptable, however, because the axial forces required for discharge of the coil 65 through the constricted region 63 will compress the coils together essentially as shown. Although not necessarily required, sealing may also be improved if the radial pitch, p2 is close to the same as the wire diameter as shown.

FIG. 3 shows a further embodiment of the inventive catheter. The catheter again has a catheter tube 52 and an inflatable balloon 54 which is formed by an inflatable sleeve 56 secured at its ends to the catheter wall in the manner described above with reference to FIG. 2. According to one aspect of the present invention, a lengthened distal section 72 is provided distal of balloon 54. At least a portion, or preferably substantially all, of distal section 72 is constricted such that the inside diameter of the catheter tube 52 in the region of distal section 72 cooperates with the outside diameter of vaso-occlusive coil 65 as it is discharged by pusher 66.

Again, pusher 66 may be on any suitable type adapted to discharge and release coil 65. Although the inventive catheter or the present invention has been described with reference to a wire type pusher, it should be appreciated that many other types of discharge devices, such as those described above, may be suitable for use with the present invention. Other types of discharge devices such as the hydraulic delivery described U.S. Pat. No. 5,669,931 to Kupiecki et al. are believed to be particularly suited for use with the present invention.

Lengthened distal section 72 is preferably heat shapeable, for instance using a shaping mandrel and steam as is known in the art. In this manner, the distal section 72 may be given any desired shape by the operating surgeon to optimize steerability for accessing the delivery site or for optimizing the fill of the aneurysm by the vaso-occlusive coil or coils. In this same manner, it may be desirable to shape the area of the catheter tube 52 in the area of the inflatable balloon 54 to facilitate optimum positioning of the balloon.

Figure 5:
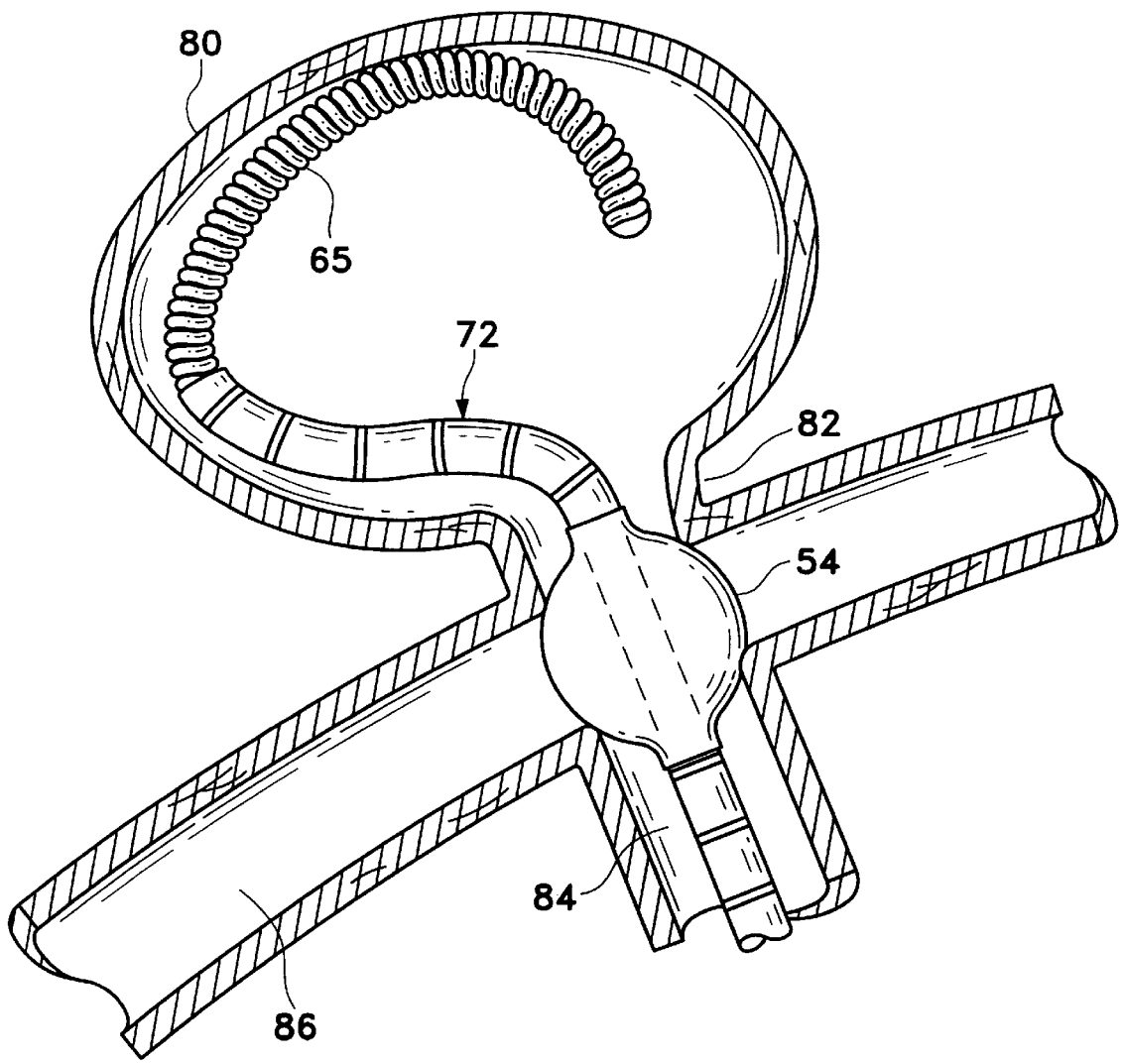
FIG. 5 is an illustration of the inventive catheter during operation at the site of a terminal aneurysm.

Referring now to FIG. 5, having a lengthened distal section is particularly useful when treating an aneurysm, such as a terminal aneurysm as shown at the intersection of terminal body lumen 84 and intersecting body lumen 86. The catheter of FIG. 3 is shown in place for delivering vaso-occlusive coil 65 with aneurysm sac 80. Distal section 72 extends through the opening at aneurysm neck 82 and into the aneurysm sac. As shown, distal section may be advantageously shaped to optimally fill the aneurysm according to the surgeon's preference and experience.

The balloon is positioned such that upon inflation, it blocks the opening of the aneurysm neck 82 to ensure that the discharged coils are contained within aneurysm sac 80 and do not escape to either the of the intersection body lumen 84, 86. The balloon is automatically inflated as the coil 65 is discharged as coil 65 cooperates with off constricted portion of the distal section 72 to seal off the catheter lumen distal of balloon 54. As coil 65 passes out of distal section 72 and completely in the aneurysm sac 80, the balloon is automatically deflated as the catheter is no longer blocked or sealed.

Referring again to FIG. 3, another aspect of the present invention involving improved radioopaque markers is illustrated. According to this aspect of the present invention, catheter tube 52 is provided with a number of variable markers both proximal to and distal to the balloon 54. Lengthened distal section 72 is provided with number of spaced radioopaque markers 73, 75, 77, 79, and 80. For delivery of vaso-occlusive coil 65 having a length, d, each distal marker has a corresponding proximal marker positioned proximally at a distance, d. For instance, proximal marker 74 is at a distance, d from distal marker 73, proximal marker 76 is at a distance, d from distal marker 75, proximal marker 78 is at a distance, d from distal marker 77, and so on with each variable marker pair spaced at a distance corresponding to the length of the coil to be delivered. Balloon markers 80, 88 may be provided to indicate the position of the balloon during the operating procedure. Pusher 66 may also be provided with tip marker 83 at its distal tip and a tail marker 98 proximally located at a distance, d which as described above corresponds to the length of the coil to be discharged.

Figure 6:
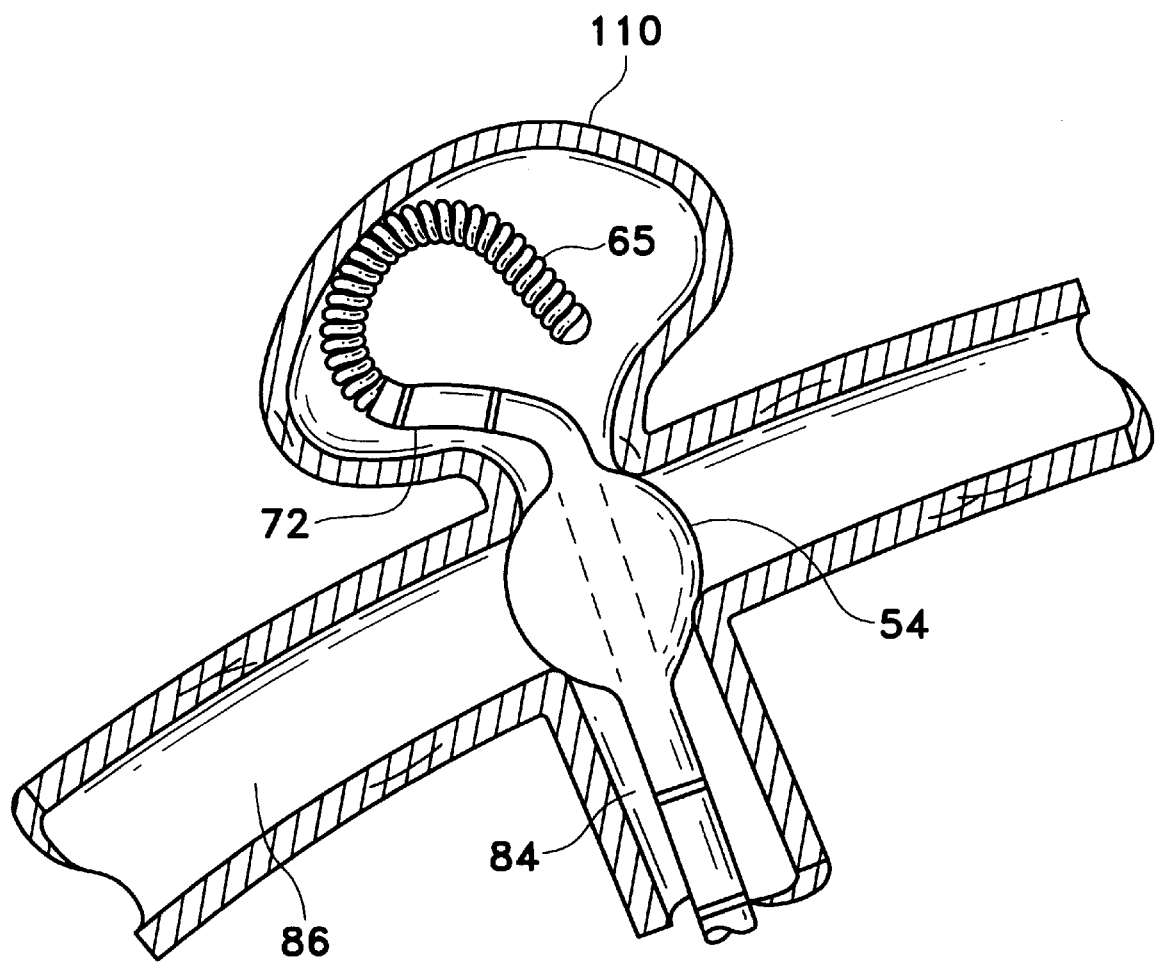
FIG. 6 is an illustration of the inventive catheter after sizing an in use at the site of a smaller terminal aneurysm.

Typically, only one of the variable marker pairs will be used for a given surgical procedure. However, the marker pairs allow the lengthened distal section 72 to be cut to a shorter length to accommodate the operating surgeon's preference. For instance, it may be desirable to have a shortened distal section 72 when accessing and treating a relatively smaller aneurysm site such as aneurysm 110 as shown in FIG. 6. In that case, distal section 72 is cut back, preferably in such a manner as to place one of the distal variable markers at or near the cut tip.

With the distal section 72 as shown in FIG. 3, the marker pair to be used would be distal marker 73 and proximal marker 74. Distal marker 73 is especially useful as the catheter is accessing the vasculature in route to and entering the delivery site or aneurysm. As a coil is loaded into the proximal end of the catheter at port 24 (FIG. 1) and advanced through the catheter distally by pusher 66, its proper position prior to discharge may be appreciated by aligning each end of coil 65 with the respective distal and proximal markers 73, 74 as shown in FIG. 3.

Once treatment of the aneurysm has begun by discharging coils into the aneurysm sac, it often becomes difficult to see distal marker 73. Proximal marker 74 may be used to determine the position of the coil. For instance, when tip marker 83 is aligned with proximal marker 74, the coil is in place to be discharged as shown in FIG. 3. When pusher 66 has been advanced until tail marker 98 is aligned with proximal marker 74 then, by virtue of the spacing of the markers, it can be determined that the coil has been fully discharged by pusher 66 and no further advancement of pusher 66 is necessary. This same procedure may be employed with any of the variable marker pairs as necessitated because the length of distal section 72 has been cut. For example, if distal section 72 is cut at location 94, distal marker 77 would be used in conjunction with proximal marker 78 in the same manner as just described with reference to marker pair 73,74.

In a preferred embodiment lengthened distal section 72 has a length of about 0.50 cm to about 3.0 cm or more. Preferably, the length of distal section 72 is about 1.0 cm to 2.0 cm. Distal markers are typically radioopaque wires or bands made from gold, tungsten, platinum, alloys of these materials, or other suitable radioopaque materials typically having a width of about 0.10 mm to about 0.50 mm. The distal markers may be placed at increments of about 2 mm to 10 mm or more, preferably about 3 mm to 7 mm.

An alternate construction of lengthened distal section is shown in FIG. 4. In some instances, having a restricted section the fill length of distal section 72 of the previous figures may result in too much friction for the delivery of very soft coils or coils whose secondary shape would tend to make them bind in such a lengthened constriction. Lengthened distal section 150, as shown in FIG. 4, is constructed similar to that of distal section 72 except that the lumen is constricted only in the location of constricting band 155. Constricting band 155 is preferably a metal band positioned over the catheter tube and held in place by heat bonding, gluing, or any number of other suitable techniques. This contruction allows a substantial portion of the distal section 150 to be radially unrestricted, thus reducing the axial force required to discharge the vaso-occlusive coil. With this construction, it may be optionally desirable to construct the distal end of the pusher (for a length equal to the length of distal section 150) with a sufficiently large diameter to engage the constriction at the band 155 so that the balloon remains inflated until the coil 65 exits the end of the catheter (otherwise the balloon deflates after the coil passes band 155 but is not yet filly discharged.).

Figure 7:
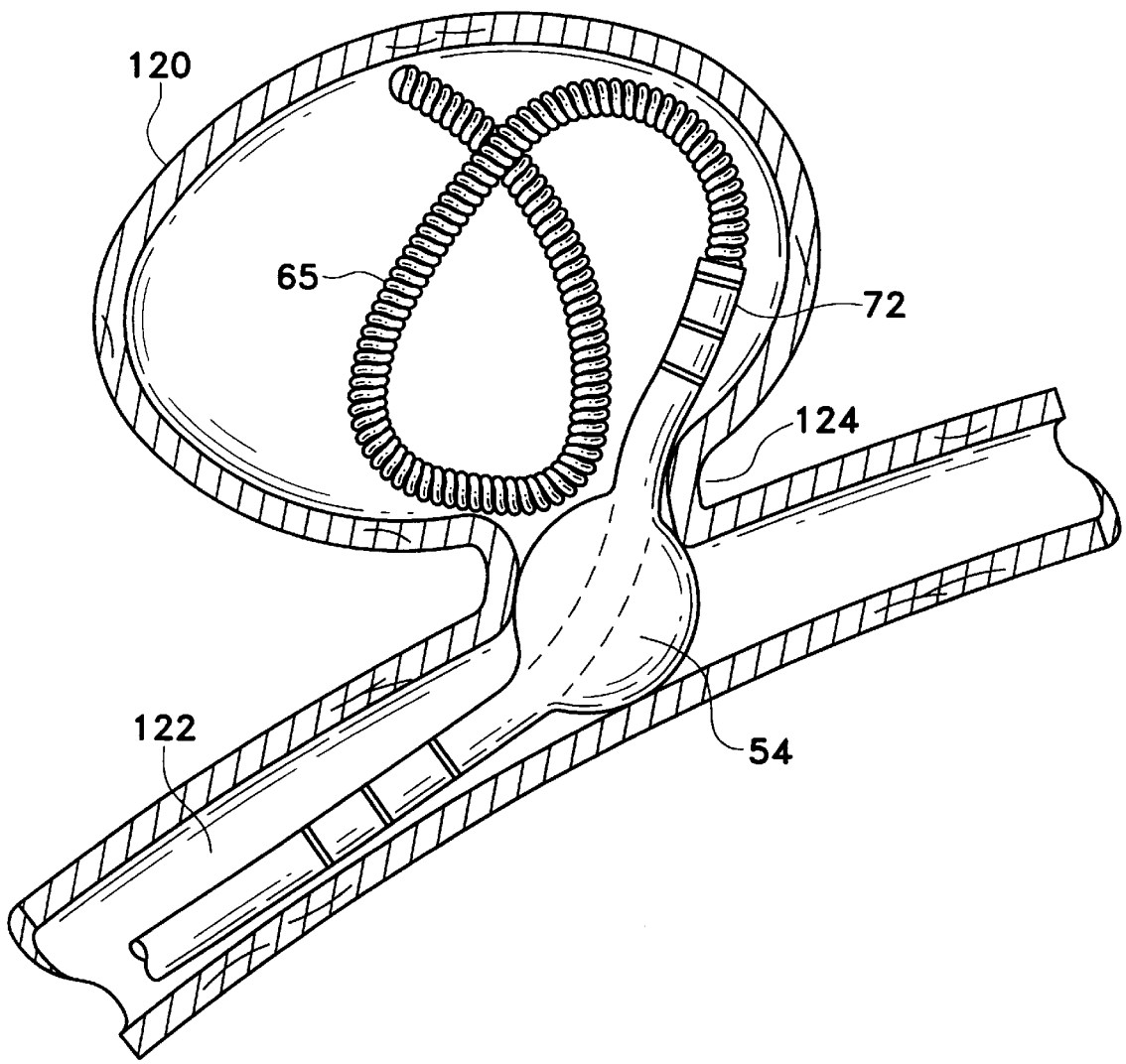
FIG. 7 is an illustration of the inventive catheter at the site of a berry aneurysm.

The inventive aspects of the catheter described in detail above are not limited solely to the treatment of terminal aneurysms as shown in the prior figures. Such devices as have been described have utility at a number of vascular sites including, but not limited to, vascular malformations, fistulas, and other types of aneurysms. FIG. 7, for example illustrates the use of the present invention with respect to berry aneurysm 120 extending from body lumen 122. Lengthened distal section 72 extends through the opening at the neck 124, but is biased against the side as shown. In this position, balloon 54 inflated as coil 65 passes through the constricted section of lengthened section 72 and is able to adequately contain coil 65 within the aneurysm.

Modification of the above-described variations of carrying out the invention that would be apparent to those of skill in the fields of medical device design generally, and vaso-occlusive delivery devices specifically, are intended to be within the scope of the following claims.

We claim as our invention:

1. A catheter assembly for delivering a vaso-occlusive member comprising;

a catheter having an inner lumen extending between proximal and distal ends, said inner lumen having an inner diameter, an inflatable balloon disposed adjacent the distal end and in fluid communication with said inner lumen, and a tip section extending from said balloon to said distal end having an inside diameter; and said vaso-occlusive member positionable within said lumen and axially slidable therein, said member having an outside diameter sized to engage said inside diameter such that said lumen is at least partially blocked, causing fluid supplied through said lumen to be forced into and inflate said balloon, said vaso-occlusive member being detachable and deliverable through said catheter distal end.

2. The catheter device of claim 1 wherein said tip section is shapeable.

3. The catheter device of claim 1 wherein said tip section further comprises a plurality of spaced radioopaque markers.

4. The catheter device of claim 3 further comprising a proximal marker for each of said spaced markers, each of said proximal markers spaced from said spaced marker by a distance substantially equal to the length of said vaso-occlusive member.

5. The catheter device of claim 4 further comprising a pusher wire having a distal end proximal to said vaso-occlusive member, said pusher being axially slidable within said lumen and having a radioopaque marker at a distance from said distal end of said pusher wire substantially equal to said length of said vaso-occlusive member.

6. The catheter device of claim 1 wherein said tip section has a length greater than 1.0 centimeter.

7. The catheter device of claim 1 wherein said inside diameter is less than or equal to said outside diameter.

8. The catheter device of claim 7 wherein said tip section is flexible.

9. The catheter device of claim 8 wherein said inside diameter is about 0.001 to about 0.003 inches less that said outside diameter.

10. The catheter device of claim 1 wherein at least at least a portion of said tip section has an inside diameter less than said outer diameter.

11. The catheter device of claim 1 further comprising an annular band positioned around the exterior of said tip section, said annular band creating an area of decreased diameter relative the area of the tip section adjacent said annular band.

12. The catheter device of claim 11 wherein said annular band is radioopaque.

13. A catheter for delivering a vaso-occlusive member, comprising:

an inner lumen extending between proximal and distal ends, said inner lumen adapted to slidably receive a vaso-occlusive coil;

a plurality of marker pairs, each of said pairs comprising a distal marker incrementally spaced from said distal end and a proximal marker, said distal and said proximal markers of each of said pairs being separated by a fixed distance.

14. The catheter of claim 13, wherein said fixed distance is substantially equal to the length of said coil.

15. The catheter of claim 13 additionally comprising an inflatable balloon in fluid communication with said lumen, said balloon being between at least one of said distal and said proximal markers.

16. The catheter of claim 13 wherein the incremental spacing is from about 2.0 mm to about 10.0 mm.

17. A method of treating a vascular malformity using a vaso-occlusive member comprising the steps of:

accessing a malformity within the body using a catheter having an inner lumen extending between a proximal and a distal end, an inflatable balloon in fluid communication with said lumen, and a distal tip section having an inside diameter, said distal tip section having a plurality of markers associated therewith;

positioning the catheter such that at least a portion of said distal tip section is within the malformity and positioning said balloon such that it will substantially occlude the opening to said malformity when it is inflated;

introducing a vaso-occlusive member into said lumen; and substantially simultaneously discharging said vaso-occlusive member from said lumen and into said malformity and occluding said lumen with said vaso-occlusive member such that the balloon is inflated.

18. The method of claim 17 wherein said malformity is a terminal aneurysm and said aneurysm is accessed through a terminal lumen.

19. The method of claim 17 wherein said malformity is a berry aneurysm.

20. The method of claim 17 additionally comprising the initial step of cutting the length of said distal tip section according to the size of the vasculature to be accessed or the size of the malformity to be treated.

21. The method of claim 17 wherein the distal tip section is constructed with a plurality of spaced radioopaque markers and the step of cutting the length further comprises cutting to the marker closest to the desired length.

* * * * *